US010646599B2

(12) United States Patent
Larsen et al.

(10) Patent No.: US 10,646,599 B2
(45) Date of Patent: May 12, 2020

(54) METHOD FOR UPREGULATING ANTIGEN EXPRESSION

(71) Applicant: Nordic Nanovector ASA, Oslo (NO)

(72) Inventors: Roy H. Larsen, Oslo (NO); Ada Repetto-Llamazares, Oslo (NO)

(73) Assignee: NORDIC NANOVECTOR ASA, Oslo (NO)

( * ) Notice: Subject to any disclaimer, the term of this patent is extended or adjusted under 35 U.S.C. 154(b) by 0 days.

(21) Appl. No.: 16/007,917

(22) Filed: Jun. 13, 2018

(65) Prior Publication Data
US 2019/0008989 A1 Jan. 10, 2019

Related U.S. Application Data

(63) Continuation of application No. 14/890,737, filed as application No. PCT/EP2014/061824 on Jun. 6, 2014, now abandoned.

(30) Foreign Application Priority Data

Jun. 7, 2013 (DK) .................................. 2013 70313

(51) Int. Cl.
*A61K 51/10* (2006.01)
*C07K 16/28* (2006.01)
*A61K 39/395* (2006.01)
*A61K 39/00* (2006.01)

(52) U.S. Cl.
CPC .... *A61K 51/1027* (2013.01); *A61K 39/39558* (2013.01); *A61K 51/1096* (2013.01); *C07K 16/2887* (2013.01); *C07K 16/2896* (2013.01); *A61K 2039/507* (2013.01)

(58) Field of Classification Search
CPC ............ A61K 51/1027; A61K 51/1096; A61K 39/39558; A61K 2039/507; A61K 51/1093; A61K 39/395; C07K 16/2896; C07K 16/2887; A61P 35/02
See application file for complete search history.

(56) References Cited

U.S. PATENT DOCUMENTS

| 6,090,365 A | 7/2000 | Kaminski |
| 2009/0274649 A1 | 11/2009 | Qu et al. |
| 2012/0315268 A1 | 12/2012 | Herting |
| 2013/0309224 A1 | 11/2013 | Heider |

FOREIGN PATENT DOCUMENTS

| WO | WO 2011/092295 A2 | 8/2011 |
| WO | WO 2013/088363 A1 | 6/2013 |

OTHER PUBLICATIONS

Lloyd et al., Protein Engineering, Design & Selection 22:159-168 (Year: 2009).*
Edwards et al., J Mol Biol 334(1): 103-118 (Year: 2003).*
Davis et al., Clinical Cancer Research 5: 611-615 (Year: 1999).*
Elgström, Erika et al., "Pattern of antigen expression in metastases after radioimmunotherapy of a syngeneic rat colon carcinoma utilizing the BR96 antibody" Experimental Hematology & Oncology, Nov. 2012, pp. 1-5, vol. 34, No. 1.
Peterson, Jerry A. et al., "Effect of Multiple, Repeated Doses of Radioimmunotherapy on Target Antigen Expression (Breast MUC-1 Mucin) in Breast Carcinomas" Cancer Research, Mar. 1997, pp. 1103-1108, vol. 57.
International Search Report for PCT/EP2014/061824 dated Jul. 28, 2014.
Tomblyn, Annals of Oncology, 2011, vol. 22, Supplement 4, p. iv192, Abstract No. 327.
Macklis, International Journal of Radiation Oncology*Biology*Physics, 2000, vol. 48, Issue 3, Supplement 1, p. 285, Abstract No. 2041.
Hernandez, Radiobiology of radioimmunotherapy: Targeting CD20 B-cell antigen in non-Hodgkin's lymphoma. International Journal of Radiation Oncology*Biology*Physics, 2004, vol. 59, issue 5—abstract.

* cited by examiner

*Primary Examiner* — Phuong Huynh
(74) *Attorney, Agent, or Firm* — Knobbe, Martens, Olson & Bear LLP

(57) ABSTRACT

The present invention relates to radioimmunoconjugates that are capable of upregulating expression of one or more antigens. The upregulated antigens can be the antigens that are targeted by the radioimmunoconjugates or different antigens expressed on the same cells. The present invention also relates to methods of treating cancer and diseases and disorders of the immune system by utilizing this enhanced expression of antigens.

5 Claims, 6 Drawing Sheets

Table 1

| Cell line | Time after end of treatment | % increase in antigen expression | |
|---|---|---|---|
| | | CD 20 | CD 37 |
| Daudi | 48 h | 45.1 | 3.8 |
| | 144 h | 48.8 | 15.1 |
| Raji | 48 h | 18.6 | 21.0 |
| Ramos | 168 h | 15.0 | 66.0 |
| Rec-1 | 48 h | 16.7 | 0 |

Fig. 3

Table 2

| Cell line | Incubation time | Time after end of treatment | % increase in antigen expression | |
|---|---|---|---|---|
| | | | CD20 | CD37 |
| Daudi | 1 h | 144 h | 5.9 | 22.0 |
| | 24 h | 48 h | 51.8 | 37.1 |
| Raji | 1 h | 168 h | 63.4 | 49.3 |

Fig. 4

Table 3

| Cell line | $^{177}$Lu-HH1 vs. DOTA-HH1 (%) | | | | $^{177}$Lu-HH-1 vs. formulation buffer (%) | | | |
|---|---|---|---|---|---|---|---|---|
| | 4 days | 8 days | 11 days | 15 days | 4 days | 8 days | 11 days | 15 days |
| Daudi | 60 | 42 | 3 | ND | 46 | 27 | 7 | 4 |
| JMV-3 | 45 | 79 | 52 | 33 | 48 | 99 | 48 | 9 |

ND- Not determined.

Fig. 5

METHOD FOR UPREGULATING ANTIGEN EXPRESSION

CROSS REFERENCE TO RELATED APPLICATIONS

This application is a continuation of U.S. application Ser. No. 14/890,737, filed on Nov. 12, 2015, which claims the benefit and priority to and is a U.S. National Phase Application of PCT International Application Number PCT/EP2014/061824, filed on Jun. 6, 2014, designating the United States of America and published in the English language, which is an International Application of and claims the benefit of priority to Danish Patent Application No. PA 2013 70313, filed on Jun. 7, 2013. The disclosures of the above-referenced applications are hereby expressly incorporated by reference in their entireties.

BACKGROUND

Field

The present invention relates to radioimmunoconjugates that are capable of upregulating expression of one or more antigens. The upregulated antigens can be the antigens that are targeted by the radioimmunoconjugates or different antigens expressed on the same cells.

The use of monoclonal antibody therapy (MAT) has been an area of great interest and strong research efforts. To be effective, MAT depends on a sufficient number of antigens per cell of which the antigens can bind to for triggering response (Sugimoto et al., 2009, Czuczman et al., 2008).

The use of radioimmunotherapy (RIT) has been approved as a therapeutic option in cancer therapy (Stevens et al., 2012). Today radioimmunotherapy is mainly used in those patient experiencing relapse from chemotherapy and/or MAT (Stevens et al., 2012).

It is known from the literature that high dose rate external beam irradiation can cause an increase of CD20 in B-cells and that this response was inhibited by antioxidants like ascorbic acid, PEG-catalase etc and enhanced by oxidation agents like $H_2O_2$ and Buthionine sulfoximine (Kunala et al., 2001; Gupta et al., 2008). It is noteworthy that the effect was lasting for only about forty-eight hours after external beam exposure.

However it was not known if low doserate radioimmunotherapy could upregulate antigen expression. In fact, Elgstrøm et al. (2012) found a reduction in antigen expression after experimental radioimmunotherapy.

Also, monoclonal antibody therapy can cause reduced expression of antigen on tumor cells (Musto et al., 2011) as well as antibody combined with chemotherapy (Hiraga et al., 2009).

Thus, it is known in the field that external beam high doserate irradiation can cause increased antigen expression and that radioimmunotherapy and monoclonal antibody therapy can cause reduced antigen expression in cancer cells.

The present standard of administration radioimmunotherapy as a reduction treatment, e.g., rituximab (the antibody) is given as a conditioning treatment before Zevalin (the radioimmunoconjugate).

A problem with this approach is that experimental work and clinical data have indicated that antibody therapy can cause antigen drift that is a selection pressure towards cells with low antigen expression, which become treatment resistant (Musto and D'Auria, 2011). This has also been indicated in experimental RIT (Elgstrom et al, 2012).

Therefore would a targeted therapeutic option that could cause the opposite, i.e., an increase of antigens on treated cells be a very valuable therapeutic tool.

SUMMARY

The present invention relates to radioimmunoconjugates that are capable of upregulating expression of one or more antigens. The upregulated antigens can be the antigens that are targeted by the radioimmunoconjugates, different antigens expressed on the same cells or a combination.

This expression allows targeting and specific inhibition of cancer cells and cells of the immune system.

Thus, one aspect of the present invention relates to a radioimmunoconjugate comprising a monoclonal antibody, an optional linker, and a radionuclide, for use in upregulating antigen expression of one or more antigens.

In one embodiment of the present invention are the one or more upregulated antigens expressed on the surface of B-cell cancer cells.

In another embodiment of the present invention is the upregulation done prior to immunotherapy or immunoconjugate therapy in a patient suffering from cancer.

In a further embodiment of the present invention is the patient suffering from a B-cell malignancy selected from the group consisting of non-Hodgkin lymphoma and chronic lymphocytic leukemia.

In yet another embodiment of the present invention is the radiolabeled monoclonal antibody HH1.

In one embodiment of the present invention is the linker a chelating linker selected from the group consisting of p-SCN-bn-DOTA, DOTA-NHS-ester, p-SCN-Bn-DTPA and CHX-A"-DTPA.

In another embodiment of the present invention is the radionuclide selected from the group consisting of $^{47}$Sc, $^{67}$Cu, $^{90}$Y, $^{105}$Rh, $^{117m}$Sn, $^{131}$I, $^{149}$Tb, $^{153}$Sm, $^{161}$Tb, $^{165}$Dy, $^{177}$Lu, $^{186}$Re, $^{188}$Re, $^{211}$At, $^{212}$Pb, $^{212}$Bi, $^{213}$Bi, $^{223}$Ra, $^{224}$Ra, $^{225}$Ac, and $^{227}$Th.

In a further embodiment of the present invention is the upregulated antigen selected from the group consisting of CD37, CD19, CD20, CD21, CD22, HLA-DR, CD23, CD39, CD52, CDw75, and CD80.

In yet another embodiment of the present invention is the radioimmunoconjugate formulated as a pharmaceutical composition.

In another embodiment of the present invention comprises the pharmaceutical composition one or more pharmaceutically acceptable carriers or adjuvants.

In a further embodiment of the present invention is the use for a combinational therapy where the radioimmunoconjugate is followed by simultaneous or post-treatment with antibody therapy, immunoconjugate therapy or a combination thereof.

In another embodiment of the present invention is the upregulated antigen CD20, and the upregulation is followed by anti-CD20 antibody therapy with rituximab in a single administration or in a repeated administration pattern.

In yet another embodiment of the present invention is the simultaneous or post-treatment targeting a different antigen than the radioimmunoconjugate.

Another aspect of the present invention relates to a method of upregulating antigen expression comprising administration of a radioimmunoconjugate to a person in which an upregulated antigen expression would be advantageous.

In one embodiment of the present invention is the person suffering from a B-cell malignancy.

In another embodiment of the present invention is the use a combinational therapy where the radioimmunoconjugate is followed by simultaneous or post-treatment with antibody therapy, immunoconjugate therapy or a combination thereof.

In another embodiment the radioimmunotherapy and immunotherapy or immunoconjugate therapy is repeated in several cycles.

In another embodiment the radioimmunotherapy is given as a low dose which by itself has a low cell kill effect in tumors, but has a significant antigen upregulation.

BRIEF DESCRIPTION OF THE DRAWINGS

FIG. 3 (Table 1) shows antigen expression increase after 1 h of incubation with $^{177}$Lu-tetulomab (BETALUTIN, anti-CD37 targeting Antibody Radionuclide Conjugate) as measured by flow cytometry.

FIG. 4 (Table 2) shows upregulation of CD20 and CD37 for cells treated with $^{177}$Lu-rituximab (BETALUTIN, anti-CD37 targeting Antibody Radionuclide Conjugate) as measured by flow cytometry.

FIG. 5 (Table 3) shows % increase in binding of $^{125}$I-rituximab to tumor cells after radioimmunotherapy vs. control 4 days/8 days/11 days/15 days after adding BETALUTIN, anti-CD37 targeting Antibody Radionuclide Conjugate, or control as measured by cell binding assay.

Figure 1:
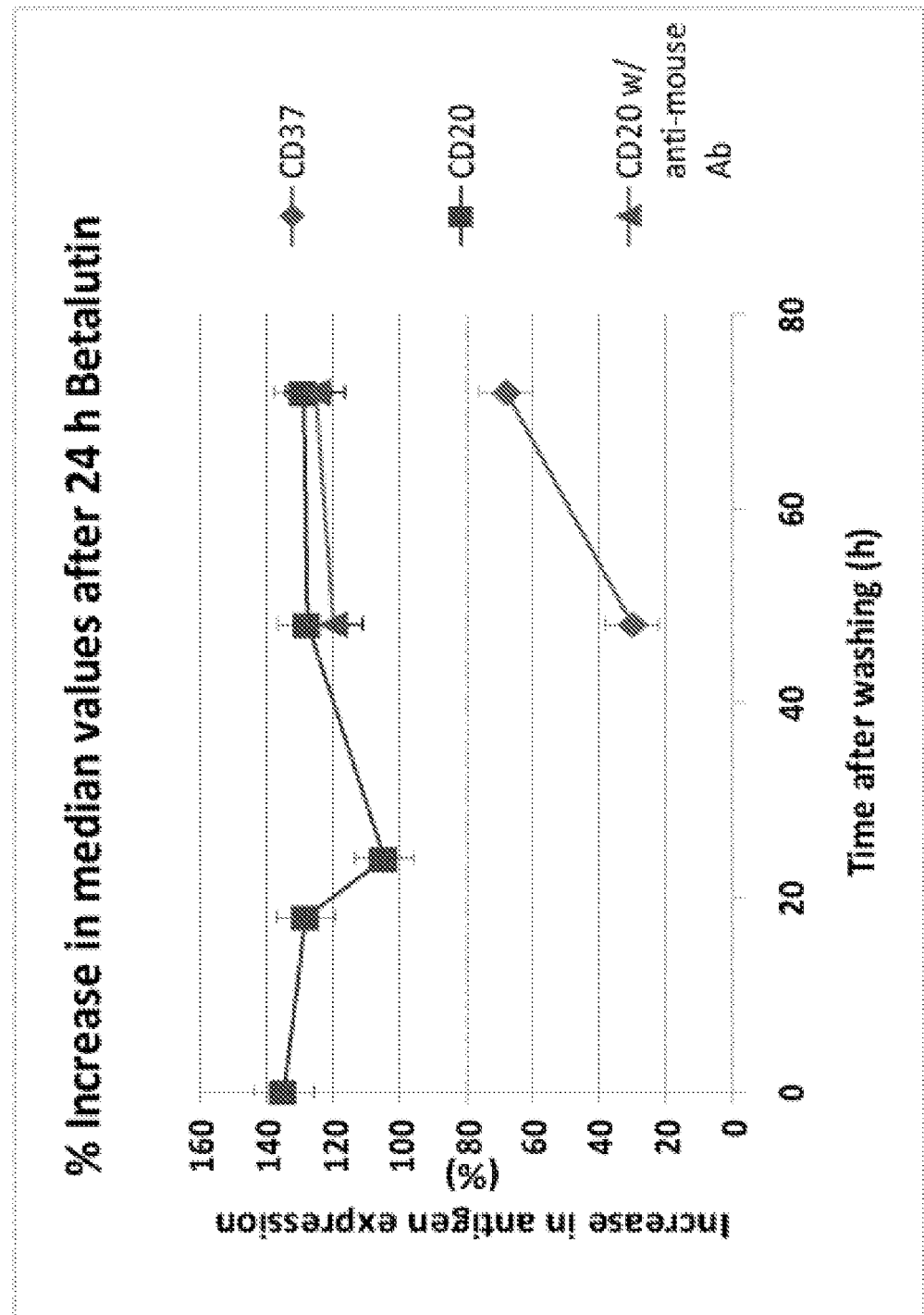
FIG. 1 shows increase in CD20 and CD37 expression for Daudi cells after 24 h incubation with BETALUTIN, anti-CD37 targeting Antibody Radionuclide Conjugate, (t=0 after removal of BETALUTIN, anti-CD37 targeting Antibody Radionuclide Conjugate, in addition of fresh medium) as measured by flow cytometry.

The present invention will now be described in more detail in the following.

DETAILED DESCRIPTION

The present inventors have to their surprise found when doing experiments with low dose rate beta emitting $^{177}$Lu-labeled HH1 antibody (also named $^{177}$Lu-tetulomab or BETALUTIN, anti-CD37 targeting Antibody Radionuclide Conjugate) against the B-cell associated antigen CD37, that cells treated with this would up-regulate the expression of both CD37 and CD20, another B-cell associated antigen.

Thus, it is shown that therapy with $^{177}$Lu-HH1 may improve condition for MAT in B-cell diseases like cancer and autoimmune disease.

It was also an unexpected finding that low dose rate radioimmunotherapy using $^{177}$Lu-HH-1 against CD37 antigen positive cells not only caused increase in antigen expression in cancer cells but also caused a prolonged effect compared to published data for external beam exposure.

The radioimmunotherapy treatment caused increased expression of both the CD37 and the CD20 antigens. This would implicate that radioimmunotherapy with, e.g., $^{177}$Lu-HH-1 could be used as an induction treatment to antibody therapy, since antibody therapy depends heavily on a good expression of the antigen.

Another noteworthy finding was that the up-regulated antigen expression could last between one and two weeks after exposure to radioimmunotherapy vs. only about two days after external beam exposure.

A new way of using targeted antibody therapy can be envisioned, i.e., induction therapy with radioimmunotherapy followed by antibody or antibody-conjugate therapy in the following days and weeks to exploit the increased antigen expression.

Thus, the present invention relates to radioimmunoconjugates that are capable of upregulating expression of one or more antigens. The upregulated antigens can be the antigens that are targeted by the radioimmunoconjugates, different antigens expressed on the same cells or a combination.

This expression allows targeting and specific inhibition of cancer cells and cells of the immune system.

Uses of Radioimmunoconjugates

Thus, one aspect of the present invention relates to a radioimmunoconjugate comprising a monoclonal antibody, an optional linker, and a radionuclide, for use in upregulating antigen expression or one or more antigens.

In one embodiment of the present invention are the one or more upregulated antigens expressed on the surface of B-cell cancer cells.

In another embodiment of the present invention will the radioimmunoconjugates of the present invention downregulate cells of the immune system.

Such cells of the immune system may be diseased such as in autoimmune diseases.

In another embodiment of the present invention is the upregulation done prior to immunotherapy or immunoconjugate therapy in a patient suffering from cancer or a disease.

In a further embodiment of the present invention the patient is suffering from a B-cell malignancy selected from the group consisting of non-Hodgkin lymphoma, acute Lymphoblastic Leukemia, and chronic lymphocytic leukemia.

In one embodiment of the present invention the patient is suffering from a B-cell malignancy that is non-Hodgkin lymphoma.

In one embodiment of the present invention the patient is suffering from a B-cell malignancy that is acute Lymphoblastic Leukemia.

In one embodiment of the present invention the patient is suffering from a B-cell malignancy that is chronic lymphocytic leukemia.

In another embodiment the radioimmunotherapy is given as a low dose which by itself has a low cell kill effect on tumors, but has a significant antigen upregulation.

In the present context is the term upregulated defined as a significantly higher expression of the antigen at protein level or mRNA level.

This inventions has surprisingly showed that a pretreatment of a B-cell malignancy using $^{177}$Lu-labeled HH1 antibody is capable of upregulating the rituximab target CD20.

Thus, one aspect of the present invention relates to the use of a combinational treatment of a B-cell malignancy using $^{177}$Lu-labeled HH1 antibody followed by rituximab.

A preferred embodiment of the present invention relates to $^{177}$Lu-labeled HH1 antibody followed by rituximab for use in the treatment of a B-cell malignancy.

This window between administration of $^{177}$Lu-labeled HH1 antibody and rituximab can be optimized to generate the maximum upregulation on CD20. The window will typically be at least one day, 3-5 days or 3-10 days.

The window may also be 0-30 days, more preferably 3-15 days after administering radioimmunotherapy. In the case of long time circulating antibodies even co- or pre-treatment may be considered as long as the antibody is present in substantial concentration in the blood at the time when antigen up-regulation take place.

Within the scope of the invention is the use of radioimmunotherapy with other radiolabeled antibodies against CD37 or other antigens associated with hematological cancer, e.g., radiolabeled anti-CD20 antibodies including ibritumomab, tositumomab, rituximab, ofatumumab, veltuzumab and ocrelizumab, or radiolabeled CD19, CD21, CD22, HLA-DR, CD23, CD39, CD52, CDw75 or CD80 antibodies including blinatumomab and epratuzumab.

Examples of radionuclides used would be $^{47}$Sc, $^{67}$Cu, $^{90}$Y, $^{105}$Rh, $^{117m}$Sn, $^{131}$I, $^{149}$Tb, $^{153}$Sm, $^{161}$Tb, $^{165}$Dy, $^{177}$Lu, $^{186}$Re, $^{188}$Re, $^{211}$At, $^{212}$Pb, $^{212}$Bi, $^{213}$Bi, $^{223}$Ra, $^{224}$Ra, $^{225}$Ac, and $^{227}$Th which can be conjugated with a chelating linker to the antibody or by electrophilic or nucleophilic reaction with groups in the protein.

Radioimmunoconjugates

The radioimmunoconjugates can be any that are capable of binding to or targeting an antigen of interest.

Radioimmunoconjugates include but are not limited to Zevalin, Bexxar and BETALUTIN, anti-CD37 targeting Antibody Radionuclide Conjugate.

In the present context is BETALUTIN, anti-CD37 targeting Antibody Radionuclide Conjugate, also referred to as $^{177}$Lu-HH1, $^{177}$Lu-HH-1, $^{177}$Lu-tetulomab or $^{177}$Lu-tetraxetan-tetulomab.

In another embodiment of the present invention will the one or more antibodies or radioimmunoconjugates target CD20.

Antibodies include but are not limited to Rituximab, Veltuzumab, Ofatumumab, Afutuzumab, Tositumomab, Reditux and Ibritumomab.

In another embodiment of the present invention will the one or more antibodies or radioimmunoconjugates target CD37.

In a preferred embodiment of the present invention is the CD37 radioimmunoconjugate BETALUTIN, anti-CD37 targeting Antibody Radionuclide Conjugate.

Antibodies

The antibodies of the present invention can be any monoclonal antibody capable of targeting any of the antigens discussed below.

Antibodies include but are not limited to Rituximab, Epratuzumab, L19, F8, F16, Galiximab, Toralizumab, Alemtuzumab, Ofatumumab, Veltuzumab, Afutuzumab, Tositumomab, Reditux, Ibritumomab, K7153A, 37.1 and HH1.

In one embodiment of the present invention is the monoclonal antibody HH1 (i.e., tetulomab).

In one embodiment of the present invention is the monoclonal antibody rituximab.

Specific variants of HH1 are disclosed in PCT/IB2012/057230 and PCT/EP2011/051231 which hereby are incorporated by reference and disclosed as specific embodiments that are included in this invention.

It will therefore be possible to adjust the variant of HH1 included in the radioimmunoconjugates of the present invention based on the above mentioned disclosures.

Such variant include chimeric variants or variants with a certain sequence identity with the chains of HH1.

In a preferred embodiment of the present invention is the variant chimeric HH1 or a humanized HH1.

In another embodiment of the present invention is the chimeric variant of HH1 chHH1.1 which is chimeric HH1 isotype IgG1 or chHH1.3H which is chimeric HH1 isotype IgG3 with R435H mutation.

In another embodiment of the present invention is the monoclonal antibody rituximab.

Linkers

The radionuclide may be attached to the antibody by an optional linker.

For example does radioimmunoconjugates with iodine not need a linker. This means that $^{125}$I-HH1 does not need to comprise a linker.

The radionuclide may be attached to the antibody by first reacting a bifunctional chelator, e.g., p-SCN-bn-DOTA (Macrocyclics, Tx, USA), with the antibody, followed by purification to remove unconjugated chelator, and then reaction of the chelator antibody conjugate with the radionuclide, followed by purification to remove any unconjugated radionuclide.

Alternatively, the chelator and the radionuclide can be combined firstly and subsequently conjugated to the antibody.

Chelating linkers like, e.g., p-SCN-bn-DOTA, can be used for conjugating other metal radionuclides to HH1 in similar fashion to that described for $^{177}$Lu.

Any type of linker with sufficient complexing ability and a functional group allowing direct or indirect conjugation to a protein or a peptide could be used. Examples of such linkers are described in the literature (e.g. Brechbiel, 2008; Liu, 2008). Some useful examples are bifunctional cyclic chelators like p-SCN-bn-DOTA, DOTA-NHS-ester; bifunctional linear chelators like p-SCN-Bn-DTPA and CHX-A"-DTPA.

The radionuclides in the present invention will preferably be conjugated to a targeting molecule by using bifunctional chelators.

These could be cyclic, linear or branched chelators. Particular reference may be made to the polyaminopolyacid chelators which comprise a linear, cyclic or branched polyazaalkane backbone with acidic (e.g. carboxyalkyl) groups attached at backbone nitrogens.

Examples of suitable chelators include DOTA derivatives such as p-isothiocyanatobenzyl-1,4,7,10-tetraazacyclododecane-1,4,7,10-tetraacetic acid (p-SCN-Bz-DOTA) and DTPA derivatives such as p-isothiocyanatobenzyl-diethylenetriaminepentaacetic acid (p-SCN-Bz-DTPA), the first being cyclic chelators, the latter linear chelators.

Metallation of the complexing moiety may be performed before or after conjugation of the complexing moiety to the targeting moiety.

The radiolabeling procedure will in general be more convenient in terms of time used etc if the chelator is conjugated to the antibody before the radiolabeling takes place.

The principles of preparing radiolabeled conjugates using chelators attached to antibodies is described broader in e.g. Liu, 2008.

Thus, HH1 can be used to prepare radioimmunoconjugates with differences in radiation properties and effective half-lives.

Thus, in one embodiment of the present invention is the linker a chelating linker selected from the group consisting of p-SCN-bn-DOTA, DOTA-NHS-ester, p-SCN-Bn-DTPA and CHX-A"-DTPA.

Beta and/or alpha-emitting radionuclides with metallic character allows complexing to bifunctional chelate linkers from the following exemplified by but not limited to Bn- TCMC, DOTA, Bn-DOTA, Bn-NOTA, Bn-oxo-DO3A, DTPA, CHX-A-DTPA, Bn-DTPA, Bn-PCTA, and molecules from the classes of calixarenes, cryptates and cryptands etc.

Thus, the linker may be a bifunctional chelating linker.

In one embodiment of the present invention is the linker a chelating linker.

Radionuclides

As mentioned above is it possible to construct radioimmunoconjugates that have different radiation properties and effective half-lives.

A natural part of constructing such radioimmunoconjugates is the choice of radionuclide.

In a preferred embodiment of the present invention is the radionuclide a metallic radionuclide.

In a further embodiment of the present invention is the radionuclide an alpha emitter.

The alpha emitter may be selected from the group consisting of $^{212}$Bi, $^{213}$Bi, $^{225}$Ac, $^{227}$Th.

In a further embodiment of the present invention is the radionuclide a beta emitter.

The beta emitter may be selected from the group consisting of $^{90}$Y, $^{153}$Sm, $^{161}$Th, $^{177}$Lu.

In another embodiment of the present invention is the radionuclide selected from the group consisting of $^{47}$Sc, $^{67}$Cu, $^{90}$Y, $^{105}$Rb, $^{117m}$Sn, $^{131}$I, $^{149}$Tb, $^{153}$Sm, $^{161}$Tb, $^{165}$Dy, $^{177}$Lu, $^{186}$Re, $^{188}$Re, $^{211}$At, $^{212}$Pb, $^{212}$Bi, $^{213}$Bi, $^{223}$Ra, $^{224}$Ra, $^{225}$Ac, and $^{227}$Th.

In yet another embodiment of the present invention is the half-life of the radionuclide less than 24 hours and the radionuclide is selected from the group consisting of $^{211}$At, $^{212}$Pb, $^{212}$Bi, $^{213}$Bi.

In another embodiment of the present invention is the half-life of the radionuclide more than 24 hours and the radionuclide is selected from the group consisting of $^{47}$Sc, $^{67}$Cu, $^{90}$Y, $^{105}$Rb, $^{117m}$Sn, $^{131}$I, $^{149}$Tb, $^{153}$Sm, $^{161}$Tb, $^{165}$Dy, $^{177}$Lu, $^{186}$Re, $^{188}$Re, $^{223}$Ra, $^{224}$Ra, $^{225}$Ac, and $^{227}$Th.

Antigens

The antigens of the present invention are antigens that can be upregulated by the radioimmunoconjugates of the present invention.

This upregulation can also be seen as an increase or induction of expression of the antigen. The upregulation or increase can be measured by conventional techniques known by the person skilled in the art including western blotting and FACS.

It may be a single antigen that is upregulated but it can also be several.

For example is it possible to upregulate both CD20 and CD37 by the radioimmunoconjugates of the present invention.

Thus, in one embodiment of the present invention is the upregulated antigen selected from the group consisting of CD37, CD19, CD20, CD21, CD22, HLA-DR, CD23, CD39, CD52, CDw75, and CD80.

In a further embodiment of the present invention is the upregulated antigen CD37.

In a yet further embodiment of the present invention is the upregulated antigen CD20.

In another embodiment of the present invention is the upregulated antigen CD22.

B-cell antigens that are upregulated by radioimmunotherapy or potentially may be up-regulated include CD19, CD20, CD22, CD37 and CD52.

Thus, in a further embodiment of the present invention are the antigens selected from the listing consisting of CD19, CD20, CD22, CD37 and CD52.

In yet another embodiment of the present invention are the B-cell specific antigens selected from the group consisting of CD19, CD20, CD22, CD37.

In a further embodiment of the present invention are both CD20 and CD37 upregulated by the radioimmunoconjugates of the present invention.

In another embodiment of the present invention are both CD22 and CD37 upregulated by the radioimmunoconjugates of the present invention.

In yet another embodiment of the present invention are both CD52 and CD37 upregulated by the radioimmunoconjugates of the present invention.

In another embodiment of the present invention are both CD19 and CD37 upregulated by the radioimmunoconjugates of the present invention.

The antigen may also be an antigen specific for auto-immune diseases or disorders.

When the antigen is specific for an auto-immune disease is the antigen downregulated and thus has the potential to treat for example inflammation.

Examples of such antigens are TNF-a, IL-2, or Immunoglobulin E.

In another embodiment of the present invention is the disease multiple myeloma and the antigen is selected from the group consisting of CD38, CD138, BCMA, CD317, CS1, CD40, BLyS, CD56, CD52, KMA, GRP78, BAFF, CXCR4, and LMA.

The antibodies involved in multiple myeloma treatment or under development for multiple myeloma treatment can be selected from the group consisting of denosumab, elotuzumab, daratumumab, milatuzumab, lucatumumab, MDX-1097, PAT-SM6, tabalumab, ulocuplumab, and MDX-1458.

Antibody drug conjugates for the treatment of multiple myeloma can be selected from the group consisting of BT062, milatuzumab-DOX, lorvotuzumab-mertansine.

Antibodies involved in osteolytic bone disease in multiple myeloma patients can be selected from the group consisting of anti-DKK-1 antibody BHQ-880 that promotes the activity of osteoblast cells that form bones.

Anti-RANKL antibody denosumab reduces the activity of osteoclasts that break down bone tissue.

Thus, in one embodiment of the present invention is the antibody denusomab and the disease is osteoporosis.

The angiogenesis antigen VEGF can be anti-VEGF antibody bevacizumab that prevents new blood vessel growth in cancer cells.

Thus, in one embodiment of the present invention angiogenesis in cancer cells is targeted, the antigen is VEGF and the antibody is bevacizumab.

Within the scope of the invention is the use of a radiolabeled antibody against one of the above mentioned myeloma antigens to induce antigen up-regulation.

Pharmaceutical Compositions

Antibodies are usually applied in the treatment of diseases formulated in pharmaceutical compositions.

Such compositions are optimized for parameters such as physiological tolerance and shelf-life.

Thus, in one embodiment of the present invention is the radioimmunoconjugate formulated as a pharmaceutical composition.

An embodiment of the present invention relates to a pharmaceutical composition as described above, further comprising one or more additional therapeutic agents.

In another embodiment of the present invention are said one or more additional therapeutic agents selected from agents that induce apoptosis.

Usually is an important element of a pharmaceutical composition a buffer solution, which to a substantial degree maintain the chemical integrity of the radioimmunoconjugate and is being physiologically acceptable for infusion into patients.

In one embodiment of the present invention the pharmaceutical composition comprises one or more pharmaceutically acceptable carriers and/or adjuvants.

Acceptable pharmaceutical carriers include but are not limited to non-toxic buffers, fillers, isotonic solutions, etc. More specifically, the pharmaceutical carrier can be but are not limited to normal saline (0.9%), half-normal saline, Ringer's lactate, 5% Dextrose, 3.3% Dextrose/0.3% Saline. The physiologically acceptable carrier can contain a radiolytic stabilizer, e.g., ascorbic acid, which protect the integrity of the radiopharmaceutical during storage and shipment.

One embodiment of the present invention comprises the pharmaceutical composition of the present invention and one or more additional antibodies or radioimmunoconjugates.

Method of Treatment

Therapeutic use of a radioimmunoconjugate according to the present invention may be for treatment against malignant cells expressing an antigen as described herein, including but not limited to a B-cell malignancy selected from the group consisting of B-cell non-Hodgkin lymphoma, B-cell chronic lymphocytic leukemia, hairy cell leukemia, lymphoplasmacytic lymphoma, acute Lymphoblastic Leukemia and multiple myeloma.

Other uses could be treatment of autoimmune diseases and treatment of transplantation related effects.

Thus, one aspect of the present invention relates to a method of upregulating antigen expression comprising administration of a radioimmunoconjugate to a person in which an upregulated antigen expression would be advantageous.

One embodiment of the present invention relates to a method of treatment of a B-cell malignancy or a disease or disorder of the immune system in which CD20 is the target and the radioimmunoconjugate is capable of upregulating CD20 antigen expression.

In a preferred embodiment of the present invention is the radioimmunoconjugate is capable of upregulating CD20 antigen expression BETALUTIN, anti-CD37 targeting Antibody Radionuclide Conjugate, and CD20 is targeted by rituximab or a variant hereof.

One aspect of the present invention relates to a combinational treatment of a B-cell malignancy or a disease or disorder of the immune system using BETALUTIN, anti-CD37 targeting Antibody Radionuclide Conjugate, followed by followed by rituximab, obinutuzumab or similar CD20 therapeutic antibody.

In one embodiment of the present invention is the person suffering from a B-cell malignancy or a disease or disorder of the immune system.

In another embodiment of the present invention is the use a combinational therapy where the radioimmunoconjugate is followed by simultaneous or post-treatment with antibody therapy, immunoconjugate therapy or a combination thereof.

The therapy could be administered either as a monotherapy or in combination with other therapies, preferentially standard treatments. Such other therapies may be pretreatment, surgery, chemotherapy (including doxorubicin, vinblastin and gemcitabine), immunotherapy, antibody therapy, photodynamic therapy, proteasome inhibitor (including bortezomib), histone deacetylase inhibitors (including vorinostat and suberoylanilide hydroxamic acid), vitamin D3 and vitamin D3 analogs, cell cycle checkpoint inhibitors (including UCN-01 and 2-(4-(4-Chlorophenoxy) phenyl)-1H-benzimidazole-5-carboxamide), hypoxic cell radiosensitizers (including metronidazole and misonidazole), apoptosis inducers (including withaferin A) radiosensitizers, radioimmunotherapy or a combination of two or more of these.

By administered is meant intravenous infusion or intravenous injection. More specifically, the radioimmunoconjugate of the present invention can be administered directly in a vein by a peripheral cannula connected to a drip chamber that prevents air embolism and allows an estimate of flow rate into the patient.

In one embodiment the radioimmunoconjugate can be administered in a repeated fashion.

In another embodiment the radioimmunoconjugate followed by monoclonal antibody (or immunoconjugate) can both be administered in a repeated fashion.

In another embodiment of the present invention the radioimmunoconjugate could be administered in a repeated fashion but with different radionuclides, e.g., beta-radioimmunotherapy could be followed by alpha-radioimmunotherapy or vice versa.

An aspect of the present invention relates to the use of the radioimmunoconjugate of the present invention for the treatment of B-cell malignancies.

An embodiment of the present invention relates to the use of the radioimmunoconjugate of the present invention administered in combination with or in addition to other therapy.

In an embodiment of the present invention the other therapies is selected from pretreatment, chemotherapy, monoclonal antibody therapy, surgery, radiotherapy, and/or photodynamic therapy.

In another embodiment of the present invention the other therapies are bone marrow transplantation or stem cell transplantation and/or therapy.

In an embodiment of the present invention the antibody dosing is 1-1000 mg per patient, more preferably 5-50 mg per patient, and $^{177}$Lu amounting to 1-200 MBq/kg, more preferably 10-100 MBq/kg of bodyweight.

Combinational Therapy

As noted above can the radioimmunoconjugates be used in combination with other types of therapy.

Thus, in a further embodiment of the present invention is the use for a combinational therapy where the radioimmunoconjugate followed by simultaneous or post-treatment with antibody therapy, immunoconjugate therapy or a combination thereof.

In another embodiment of the present invention is the upregulated antigen CD20, and the upregulation is followed by anti-CD20 antibody therapy with rituximab in a single administration or in a repeated administration pattern.

It is therefore possible to use the present radioimmunoconjugates to upregulate other antigens than the antigen the radioimmunoconjugates target.

Thus, in yet another embodiment of the present invention is the simultaneous or post-treatment targeting a different antigen than the radioimmunoconjugate.

The administration pattern can be in a single administration where the radioimmunoconjugates upregulate and expression of one or more antigens which then are targeted by a single dose or several doses of antigen-specific therapy.

Such therapy may be a monoclonal antibody such as rituximab or HH1 depending on the antigen in focus.

The therapy can be repeated in cyclic pattern where administration of the radioimmunoconjugates and the monoclonal antibodies are repeated once, twice or several times.

An advantage of such administration is that the target cell can be treated by the same or different antibodies in each cycle ensuring that the antigen with the highest expression is in focus.

A strategy where several antigens are in focus limits the risk of expressional drifting of the antigens expressed on the surface of the target cells.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Treatment with BETALUTIN, Anti-CD37 Targeting Antibody Radionuclide Conjugate ($^{177}$Lu-Tetraxetan-Tetulomab, or $^{177}$Lu-HH1) and Effect on Antigen Expression Materials & Methods:
Labelling of Antibodies Labelling of the antibody HH-1 with p-SCN-Bn-DOTA and $^{177}$Lu was performed following standard procedures described in Dahle et al. (2013) and Repetto-Llamazares et al. (2013). The radiochemical purity (RCP) of the radioimmunoconjugate (RIC) was evaluated using Instant Thin Layer Chromatography. If RCP was below 95% the conjugate was purified using Econo-Pac 10 DG columns (Bio-rad Laboratories, California, USA). RCP was higher than 97% for all RICs used in the experiments. The specific activity of BETALUTIN, anti-CD37 targeting Antibody Radionuclide Conjugate, was 92 MBq/kg with an antibody concentration of 178 µg/ml. The immunoreactive fractions (IRFs) of the RICs were estimated using Ramos and Daudi lymphoma cells and a one point assay. A cell concentration of 75 million cells/ml were used. Cells incubated with cold tetulomab were used to assess the non-specific binding. Blocked and unblocked cells were incubated for 1.5 h with 40 ng/ml of radioimmunoconjugate. The added activity was measured using by a calibrated gamma detector (Cobra II auto-gamma detector, Packard Instrument Company, Meriden, Conn., USA). Cells were afterwards washed three times with PBS with 0.5% BSA and bound activity was measured in the gamma counter. IRF was estimated by subtracting the non-specific binding measured using the blocked samples to the bound activity of the unblocked samples. The IRF was 52+/−3 in Daudi cells and 75+/−1 in Ramos cells.

Labelling of rituximab with Alexa 647 was done using the corresponding Alexa Fluor Protein Labeling Kit (Molecular Probes, Life Technologies) according to the procedure provided by the manufacturer.

Treatment of Cells

On day 0, Daudi cells were diluted to 1 million cell/ml using RPMI 1640 supplied with 10% FBS. Cells were then aliquoted in two cell culture flasks, each containing 6 ml. One of the flasks received around 4.6 MBq of $^{177}$Lu-tetraxetan-tetulomab (10 µg/ml) while the other didn't receive any treatment. Both flasks were incubated for 24h, washed and resuspended in fresh medium to a concentration of 0.5 million cells/ml. The absorbed radiation dose to the medium of the treated cells was around 1.1 Gy. Both treated and control cells were then aliquoted in cell culture flasks that corresponded to each time point to be measured. Each cell flask contained around 5 ml of cell suspension. Fresh medium was not given to the cells until the end of the experiment 72 h after treatment.

Flow Cytometry Measurements

At each time point control cells where stained with 0.4 µg/ml of the DNA stain Hoechst33342 (H33342) for 20 minutes at 37° C. Subsequently, control and treated cells were washed and mixed. Cells were incubated for 20 minutes with cold tetulomab in order to saturate all CD37 sites. Subsequently cells were washed with PBS and the anti-CD20 antibody rituximab conjugated to Alexa647 and a secondary rabbit anti-mouse antibody (conjugated to phycoerythrin (PE) (DakoCytomation) were added to the solution. After incubation in ice for 30 minutes samples were washed and measured using flow cytometry. The increase in antigen expression (CD37 or CD20) was calculated as the difference in intensity measurements (in %) between the control and the treated cells. The control and treated cells were distinguished by gating on the blue fluorescence from the H3342 stain in the control cells' DNA. CD20 upregulation was evaluated for 0, 18, 24, 48 and 72 hours. CD37 was evaluated at 24 and 48 h. To control that the rabbit anti-mouse Ab didn't influenced the CD20 measurements, staining with and without the anti-mouse Ab was performed at 24 h and 48 h.

Results:

There was an increase in CD20 expression by around 130% vs. untreated control for most time points (FIG. 1). There was an increase in CD37 expression of around 60% (FIG. 1). There was no interaction between rituximab and the rabbit anti-mouse antibody since the increase in CD20 expression in samples with and without rabbit antibody was similar.

Conclusion:

The CD20 and CD37 antigens were up-regulated after cells were treated with $^{177}$Lu-tetraxetan-tetulomab. The increase was approximately constant for all time points and around 130% for CD20 and it increased from 30 to 60% for CD37 between 48 and 72 h after treatment.

Example 2

Introduction

To evaluate if the effect from $^{177}$Lu-tetulomab was due to cell specific radiation, Daudi cells were incubated with BETALUTIN, anti-CD37 targeting Antibody Radionuclide Conjugate, for 1 h.

Materials and Methods
Labelling of Antibodies

The procedure used to label the antibodies and to calculate the IRF has been previously discussed in Example 1. The specific activity of $^{177}$Lu-tetulomab was 212 MBq/mg and the Ab concentration was 0.5 mg/ml. The IRF was 72+/−2% and it was measured in Ramos cells.

Treatment of Cells

The procedure followed to treat the cells was similar to the one described in example 1. Two different treatments were evaluated in this example. One treatment involved incubation of cells during 24 hours, similarly to what was done in example 1. The other treatment involved incubation of cells during 1 hour. Control cells were prepared for each of the treatments as described in example 1. The same amount of activity was added to both treatments (4.6 MBq, the same activity as given in example 1). Every 2 to 5 days cells were split and fresh medium was added so that the cell concentration was between 0.5 and 1 million cells/ml after dilution.

Flow Cytometry Measurements

The staining of cells and measurement of antigen upregulation in treated cells compared to control cells was performed using the same procedure as described in example 1. Measurements were performed at time points between 0 and 14 days.

Results

Figure 2:
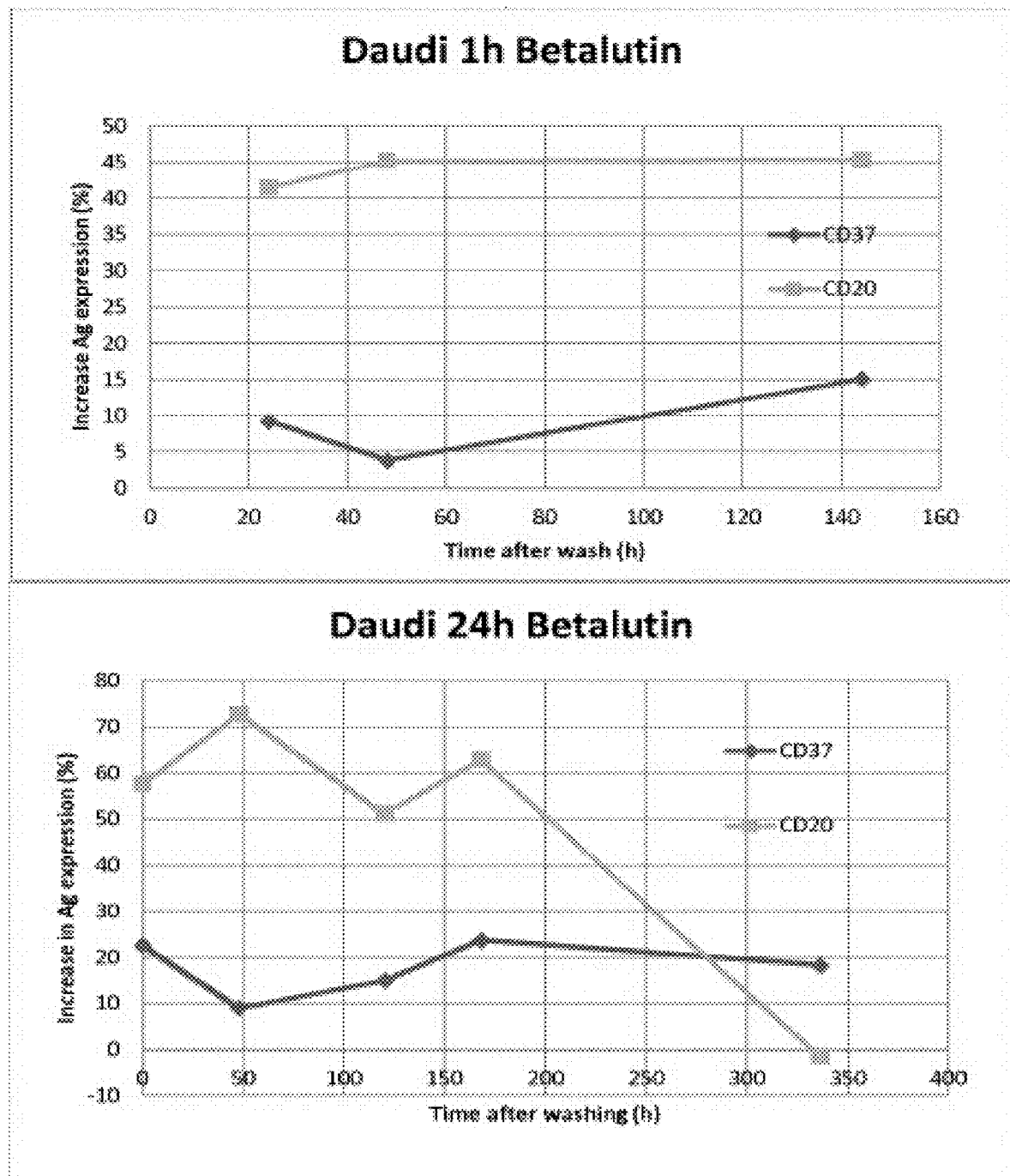
FIG. 2 shows upregulation of CD37 and CD20 for Daudi cells incubated during 1 h and 24 h with $^{177}$Lu-tetulomab (BETALUTIN, anti-CD37 targeting Antibody Radionuclide Conjugate) as measured by flow cytometry.

The dose to the medium of the cells incubated for 1 h was around 0.05 Gy while the dose to the cells incubated during 24 hours was around 1.1 Gy. Cells incubated for 1 h had 45.5% increase in CD20 and 3.8% increase in CD37 48 h after exposure and 48.8% and 15.1% respectively 144 h after exposure indicating that cell specific radiation from the radioimmunoconjugate was an important component to the effect, particularly for the CD20 antigen (FIG. 2).

Upregulation of antigens seems to decrease towards 0 after 14 days.

Example 3

Introduction

To study if the upregulation of antigens was a general feature of lymphoma rather than a cell line specific effect, Daudi cells were tested together with the three other lymphoma cells lines, Raji, Ramos and Rec-1.

Materials and Methods

Labelling of Antibodies

The procedure used to label the antibodies and to calculate the IRF has been previously discussed in Example 1. The specific activity of $^{177}$Lu-tetulomab was 212 MBq/mg and the Ab concentration was 0.5 mg/ml. The IRF was 72+/−2% and it was measured in Ramos cells.

Treatment of Cells

The procedure followed to treat the cells was similar to the one described in example 1. Cells were incubated during 1 hour. Control cells were prepared for each of the cell lines as described in example 1. The same amount of activity was added to the cell lines (4.6 MBq, the same activity as given in example 1). The dose to the medium of the cells was around 0.05 Gy. Every 2 to 5 days cells were split and fresh medium was added so that the cell concentration was between 0.5 and 1 million cells/ml after dilution.

Flow Cytometry Measurements

The staining of cells and measurement of antigen upregulation in treated cells compared to control cells was performed using the same procedure as described in example 1. Measurements were performed at time points between 0 and 7 days.

Results

The upregulation of antigens seems to be general for non-Hodgkin lymphoma cells. The increase in CD20 was observed on all cell lines while increase in CD37 expression was observed on 3 of the 4 cells lines (Table 1). In conclusion exposure to the $^{177}$Lu-tetulomab radioimmunoconjugate causes increases in CD20 and CD37 and this seems to be a general feature of B-cell lymphomas.

Example 4

Effect on Antigen Expression from Targeting CD20 with 177Lu-Rituximab

Introduction

To study if the effect was a general feature of radioimmunoconjugates rather than a specific effect of BETALUTIN, anti-CD37 targeting Antibody Radionuclide Conjugate, (i.e., $^{177}$Lu-HH-1 or $^{177}$Lu-tetulomab), Daudi and Raji cells were treated with $^{177}$Lu-rituximab.

Materials and Methods

Labeling of Antibodies

The procedure used to label rituximab and to calculate the IRF has been previously discussed in Example 1. The specific activity of $^{177}$Lu-rituximab was 165 MBq/mg and the Ab concentration was 0.2 mg/ml. The IRF was 60+/−2% and it was measured in Ramos cells.

Labelling of tetulomab with Alexa 488 was done using the corresponding Alexa Fluor Protein Labeling Kit (Molecular Probes, Life Technologies) according to the procedure provided by the manufacturer.

Treatment of Cells

The procedure followed to treat the cells was similar to the one described in example 1. Cells were incubated during 1 hour or 24 hours. Daudi and Raji lymphoma cells were used. Control cells were prepared for each of the cell lines as described in example 1. The same amount of activity was added to the cell lines (4.6 MBq, the same activity as given in example 1). The dose to the medium of the cells was around 0.05 Gy. Every 2 to 5 days cells were split and fresh medium was added so that the cell concentration was between 0.5 and 1 million cells/ml after dilution.

Flow Cytometry Measurements

The staining of cells and measurement of antigen upregulation in treated cells compared to control cells was performed using the same procedure as described in example 1. Measurements were performed at time points between 0 and 7 days. Given that $^{177}$Lu-rituximab binds to CD20 and that the same antibody was used to measure the intensity of fluorescence, the results found give a minimum value for the upregulation of CD20. The upregulation of CD37 was evaluated by using both secondary (rabbit anti-mouse) and direct Ab (tetulomab bound to Alexa488).

Results

Upregulation in CD20 and CD37 was observed also when cells are treated with $^{177}$Lu-rituximab (Table 2). Thus the upregulation of antigens is not a specific effect of $^{177}$Lu-tetulomab.

Example 5

Introduction

To confirm that radioimmunotherapy would increase the antibody binding to cells in a different assay, the two cell lines Daudi (Non-Hodgkin lymphoma) and JMV-3 (B-cell leukemia) were treated with $^{177}$Lu-HH-1 (anti-CD37) and subsequently the binding of $^{125}$I-Labeled rituximab (anti-CD20) was measured.

Methods:

$^{125}$I-rituximab was prepared using iodogen tubes (Pierce). An iodogen tube was washed with 1 ml tris-buffer and subsequent added 100 µl tris buffer (pH 7.5) and added $^{125}$I iodine. The solution was swirled gently in the tube a few times during a 6 minutes period where after some or all of the $^{125}$I solution was added to a vial with typically 100 µl tris with 50-200 µg OI-3 antibody.

Using occasional swirling of the vial, the reaction went on for 7 minutes. After that 50 µl 1-tyrosine (saturated) in tris was added and reacted for at least 5 minutes before the solution was purified using a Sephadex G-25 PD-10 (GE Health) gel filtration column.

About 70% of the activity would elute in the high molecular weight fractions and was collected and used in cell binding experiment.

The antibody HH-1 was first labeled with p-SCN-Bn-DOTA dissolved in 0.005M HCl. The molar ratio of p-SCN-Bn-DOTA to antibody was 6:1. The reaction was pH-adjusted to 8.5±0.2 using carbonate buffer. After 45 minutes of incubation at 37° C. the reaction was stopped by the addition of 50 µl of 0.2 M glycine solution/mg of Ab. To remove free chelator the conjugated antibody was washed by diluting the antibody conjugate 1:10 with 0.9% NaCl and up-concentrate by centrifugation with AMICON-30 centrifuge tubes (Millipore, Cork, Ireland). The procedure was repeated 4-5 times. Before labeling with 220 MBq $^{177}$Lu (Perkin Elmer, Boston, Ma, USA), 1 mg of antibody conjugate the pH was adjusted to 5.3±0.3 using 0.25 M Ammonium Acetate buffer. The reaction was incubated for 15 minutes at 37° C.

The radiochemical purity (RCP) of the radioimmunoconjugate (RIC) was evaluated using instant thin layer chromatography (ITLC). The RCP was 95.5%. The immunoreactive fractions (IRFs) of the RICs were measured using Ramos ($^{177}$Lu-HH1) or Daudi ($^{125}$I-Rituximab) lymphoma cells and a one point assay. A cell concentration of approximately 50 million cells/ml were used. Two tubes were not blocked and 2 tubes were pretreated with 10 µg HH-1 whereafter they were added 2 ng of $^{177}$Lu-HH1 and shaken for 1.5 hours. Thereafter the tubes were counted on a gamma counter to determine applied activity, washed and centrifuged three times with 0.5 ml DPBS/BSA before the tubes were counted for cell bound activity. The cell bound activity was corrected for non-specific binding by subtracting the counts from the blocked tubes. The IRF, i.e., specific bound vs. total applied, was 78% ($^{177}$Lu-HH1) and 71% ($^{125}$I-rituximab). Cell culture flasks (25 cm2, Corning) containing 5 ml of RPMI 1640 supplied with 10% FBS and with 1 million cells per ml were added either 2.5 MBq $^{177}$Lu-Bn-DOTA-HH-1 ($^{177}$Lu-HH-1), Bn-DOTA-HH-1 (DOTA-HH-1, control group 1) or formulation buffer, i.e., same solution as the two other treatment except for RIC or antibody conjugate (control group 2) in 16.7 microliter. After one day 2 ml was withdrawn and 3 ml fresh medium was added (1.7 times dilution), after three days the 3 ml medium was added (1.5 times dilution), after five days 4 ml was withdrawn and 3 ml fresh medium was added (1.8 times dilution), at day eight 6 ml was withdrawn and 5 ml of fresh medium was added (2.7 times dilution), at day eleven, 7 ml was withdrawn and 4 ml fresh medium added (5 times dilution). This was done to resupply with growth medium and to simulate the reduction in concentration with time seen in vivo with RICs.

After 3.5 days the cells suspensions were withdrawn and cell concentration and viability was measured using a Countess automated cell counter (Invitrogen) and 0.5 ml were added to reaction tubes centrifuged and the cell pellet re-suspended in 200 µl DPBS (Gibco) with 0.5% BSA (VWR). Two tubes in the $^{177}$Lu-HH-1 group were added 0.8 Mg, i.e. approximately 1.6 µg/ml $^{125}$I-rituximab in 10 µl DPBS/BSA and two tubes were added only DPBS (to correct for counting interference from $^{177}$Lu in the $^{125}$I window). Two tubes in control group 1 and 2 were added 0.8 Mg, i.e. approximately 1.6 $^{125}$ 1-rituximab in 10 µl DPBS/BSA and 10 µl DPBS/BSA buffer. The tubes were incubated for 1.5 hours and thereafter washed and centrifuged twice before counted in the $^{125}$I window of a Cobra II Autogamma (Packard) gamma counter. The counts in the $^{177}$Lu-HH-1 group were corrected for crossover counts from $^{177}$Lu to in $^{125}$I window by using the measurements from the two tubes not added $^{125}$I-rituximab.

Results

Cell bound activity was adjusted for cell number and $^{177}$Lu interference in the $^{125}$I window and comparisons between RIC treated and non-treated controls 1 (the antibody conjugate except the $^{177}$Lu) and 2 (the buffer solution of the RIC) are presented in Table 3. It is shown that cells treated with RIC had increased binding of $^{125}$I-Rituximab at all time points up to and including 15 days after starting therapy with $^{177}$Lu-HH1.

Conclusion

As shown in table 3 both b-cell lymphoma and b-cell leukemia cells showed increased binding of $^{125}$I-rituximab after $^{177}$Lu-HH1 exposure. This indicates that radioimmunotherapy could be beneficial as induction therapy in patients undergoing monoclonal antibody therapy, e.g., rituximab treatment against lymphoma and leukemia.

Example 6

Evaluation of Non-Specific Binding

Background

To verify that the increased binding of antigen specific antibody to cells exposed to radioimmunotherapy was not caused by increased non-specific binding to the cells an experiment using antigen blocking was performed.

Experimental:

Daudi cells, approximately 1 million per ml in 25 cm$^2$ culture flasks, were exposed to either unlabeled HH1 antibody (control 1), formulation buffer (control) or 0.1 MBq/ml or 0.5 MBq/ml $^{177}$Lu-HH-1 for three days. After one day the concentration was reduced to 50% by adding fresh medium. At day three the cells suspensions were withdrawn and used for the binding assay and treated as in example 4, with duplicate tubes from the tree groups receiving $^{125}$I-rituximab. In addition duplicates of each group was treated with unlabeled rituximab (100 µg/ml) for half an hour to block the CD20 antigen. To correct for $^{177}$Lu in $^{125}$I window duplicates from the two radioactive groups were used without added $^{125}$I-rituximab and treated and washed the same way as the test tubes with $^{125}$I-rituximab. After addition of $^{125}$I-rituximab, the test tubes were incubated for two hours and counted for applied activity. A Cobra II auto gamma counter (Packard Instruments Company Inc., Downers Grove, Ill., USA) was used. Thereafter, the test tubes were twice washed with DPBS/0.5% BSA and centrifuged twice and counted for cell bound activity. Data were corrected for gamma spillover into the $^{125}$I window from $^{177}$Lu in the treated cells.

Results:

When comparing net activity counts per cell in the blocked vs. unblocked tubes the results were as follows: 0.1 and 0.5 MBq/ml groups, 0.8% and 1.1% nonspecific binding; Controls 1 and control 2, 1.3% and 1.1% nonspecific binding.

Conclusion:

The antigen blocking was equally effective on treated and not-treated cells. Thus the increased binding to radioimmunoconjugate treated cells was not caused by non-specific binding and must therefore be caused by increased antigen expression.

Example 7

Treatment with BETALUTIN, Anti-CD37 Targeting Antibody Radionuclide Conjugate ($^{177}$Lu-Tetraxetan-Tetulomab, or $^{177}$Lu-HH1) and Effect on CD20 Antigen Expression In-Vivo This example verifies that the antigen upregulation effect from $^{177}$Lu-HH1 is also observed in-vivo. Biodistributions and tumor uptake in nude mice bearing subcutaneous Ramos xenografts was measured 3 days after treatment with BETALUTIN, anti-CD37 targeting Antibody Radionuclide Conjugate, or with a control injection of cold HH1.

Method:
Labeling Tetulomab with $^{177}$Lu

The chelator p-SCN-Bn-DOTA (DOTA) was dissolved in 0.005 M HCl, added to the antibody in a 6:1 ratio and pH-adjusted to approximately 8.5 using carbonate buffer. After 45 minutes of incubation at 37° C. the reaction was stopped by the addition of 50 µl per mg of Ab of 0.2 M glycine solution. To remove free DOTA the conjugated antibody was washed using AMICON-30 centrifuge tubes (Millipore, Cork, Ireland) 4-5 times with NaCl 0.9%. Before labeling with $^{177}$Lu the pH was adjusted to 5.3±0.3 using 0.25 M ammonium acetate buffer. Around 150 MBq of $^{177}$Lu (Perkin Elmer, Boston, Ma, USA) were added to 0.5 mg of DOTA-Ab, and incubated during 20 minutes at 37° C. Specific activity was 250 MBq/mg. The radiochemical purity (RCP) of the conjugate was evaluated using instant thin layer chromatography. If RCP was below 95% the conjugate was purified using Econo-Pac 10 DG columns (Bio-rad Laboratories, California, USA).

Labeling rituximab with $^{125}$I

Rituximab was labeled with $^{125}$I through indirect iodination using IODOGEN pre-coated iodination tubes (Pierce, Rockford, Ill.) according to manufacturer's description. After terminating reaction with L-tyrosine, the reaction mixture was eluted through Sephadex G-25 PD-10 column to remove low-molecular weight compounds. The specific activity of the final product was 12 MBq/mg.

Immunoreactive Fraction of $^{177}$Lu-HH1 and $^{125}$I-Rituximab

Single cell suspensions of Ramos lymphoma cells were grown in RPMI 1640 medium (PAA, Linz, Austria) supplemented with 10% heat-inactivated FCS (PAA), 1% L-glutamine (PAA) and 1% penicillin-streptomycin (PAA) in a humid atmosphere with 95% air/5% CO2. The immunoreactivity of the radioimmunoconjugates was measured using a one point modified Lindmo method. The cell concentrations used was 75 million cells/ml. The immunoreactivity of the conjugates was between 60% and 82%.

Animals

Institutionally bred female athymic nude Foxn1nu mice that were around 8-9 weeks old and had body weights around 22 g at the start of the experiment were used. The animals were maintained under pathogen-free conditions, and food and water were supplied ad libitum. All procedures and experiments involving animals in this study were approved by the National Animal Research Authority and carried out according to the European Convention for the Protection of Vertebrates Used for Scientific Purposes. Mice were injected subcutaneously in both flanks with 50 µl of a mushed solution of Ramos lymphoma tumor tissue slightly diluted with around 300 µl NaCl for each ml of mushed tumor solution.

Biodistribution Uptake Experiments

The biodistribution of $^{125}$I-rituximab and $^{177}$Lu-HH1 were determined in nude Foxn1nu mice with Ramos xenografts with diameters between 5 and 14 mm at the start of the study. The preparations were administered by tail vein injection of 100 µl solution to each animal. A dosage of around 350 MBq/kg of BETALUTIN, anti-CD37 targeting Antibody Radionuclide Conjugate, equivalent to a protein dosage of 2.3 mg/kg (the $^{177}$Lu-HH-1 had been stored before use hence the specific activity was reduces) was administered to 5 mice (treated mice). The control group consisted in 7 mice which were injected with the same protein dosage of cold HH1 as the treated ones (2.3 mg/kg). Two days after injection of BETALUTIN, anti-CD37 targeting Antibody Radionuclide Conjugate, or cold HH1, all mice were injected with 3 mg/kg of $^{125}$I-rituximab. Three days after injection of $^{125}$I-rituximab mice were euthanized by cervical dislocation and autopsies were performed. The weight of each tissue sample was determined, and the amount of $^{177}$Lu and $^{125}$I was measured by a calibrated gamma detector (Cobra II auto-gamma detector, Packard Instrument Company, Meriden, Conn., USA). Samples of the injectates were used as references in the measurement procedures. The decay corrected percentages of the injected dose per gram tissue (% ID/g) were calculated for each time point. Activity in organs was measured by using a dual window setting were $^{177}$Lu and $^{125}$I activities were measured simultaneously. Blank tubes with either $^{177}$Lu or $^{125}$I alone were used to assess the cross over from the windows. Cross over from $^{125}$I window to $^{177}$Lu window was around 0.006% and was considered negligible. On the other hand, cross over from $^{177}$Lu window to $^{125}$I window was around 10% and all data was corrected accordingly. In addition samples were left to decay for 10 weeks (around 10 $^{177}$Lu half-lives) and counted again to corroborate the efficacy of the corrections.

Figure 6:
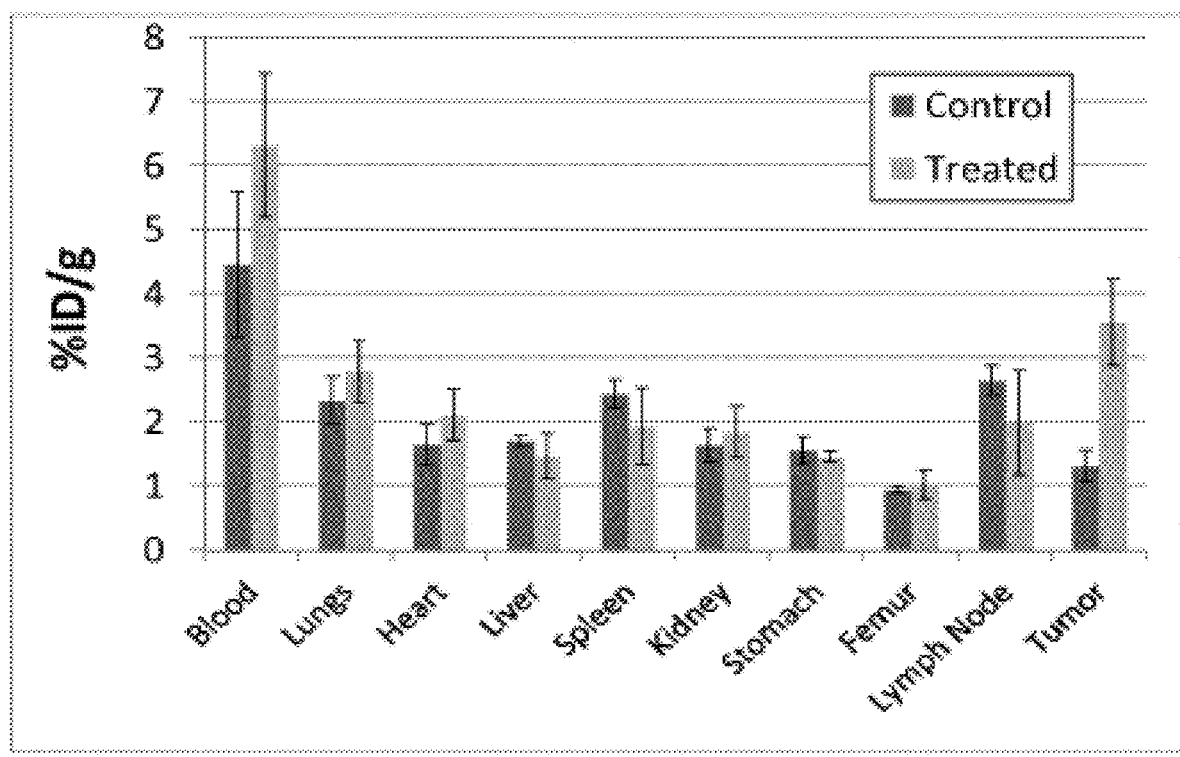
FIG. 6 shows biodistribution of $^{125}$I-rituximab 3 days after injection of $^{125}$I-rituximab. Mice had been injected 5 days earlier either with 350 MBq/kg BETALUTIN, anti-CD37 targeting Antibody Radionuclide Conjugate (treated) or cold HH1 (control).

Results:

FIG. 6 shows the biodistribution of $^{125}$I-rituximab 3 days after injection of $^{125}$I-rituximab. Mice had been injected 5 days earlier either with 350 MBq/kg BETALUTIN, anti-CD37 targeting Antibody Radionuclide Conjugate (treated) or cold HH1 (control). Uptake in normal organs was similar in both groups (p>0.05) while uptake in tumor was around 3 times higher in the treated mice (p=3.19 10-10). Avg % ID/g in tumor in control mice was 1.3+/−0.2 while it was 3.6+/−0.7 in treated mice.

Conclusions:

Treatment with BETALUTIN, anti-CD37 targeting Antibody Radionuclide Conjugate, increased the tumor uptake by 3 times while keeping uptake in normal organs constant as compared with mice treated with cold HH1. These results together with the data shown in previous examples indicate that treatment with BETALUTIN, anti-CD37 targeting Antibody Radionuclide Conjugate, upregulates the CD20 antigen in vivo and this translates into a substantially increased tumor uptake.

What is claimed is:

1. A method of sensitizing B-cell cancer cells in a person for an anti-CD20 drug comprising:
   administering to a person having B cell cancer cells, $^{177}$Lu-tetulomab ($^{177}$Lu-HH1), and
   administering rituximab to said person 3-15 days after administration of the $^{177}$Lu-tetulomab ($^{177}$Lu-HH1), wherein the $^{177}$Lu-tetulomab ($^{177}$Lu-HH1) increases CD20 antigen expression in cancer cells.

2. The method of claim 1, wherein said person has a B-cell malignancy selected from the group consisting of non-Hodgkin lymphoma, acute Lymphoblastic Leukemia, and chronic lymphocytic leukemia.

3. The method of claim 1, wherein said $^{177}$Lu-tetulomab ($^{177}$Lu-HH1) further comprises a linker.

4. The method of claim 3, wherein the linker is a chelating linker selected from the group consisting of p-SCN-bn-DOTA, DOTA-NHS-ester, p-SCN-Bn-DTPA and CHX-A-DTPA.

5. The method of claim 1, wherein the $^{177}$Lu-tetulomab ($^{177}$Lu-HH1) is formulated as a pharmaceutical composition.

* * * * *